United States Patent [19]

Himmler et al.

[11] Patent Number: 5,659,038

[45] Date of Patent: Aug. 19, 1997

[54] 5-VINYL-AND 5-ETHINYL-QUINOLONE- AND -NAPHTHYRIDONE-CARBOXYLIC ACIDS

[75] Inventors: Thomas Himmler, Odenthal; Uwe Petersen, Leverkusen; Klaus-Dieter Bremm, Recklinghausen; Rainer Endermann, Wuppertal; Michael Stegemann; Heinz-Georg Wetzstein, both of Leverkusen, all of Germany

[73] Assignee: Bayer Aktiengesellschaft, Leverkusen, Germany

[21] Appl. No.: 642,662

[22] Filed: May 3, 1996

Related U.S. Application Data

[62] Division of Ser. No. 398,328, Mar. 3, 1995, Pat. No. 5,578,604.

[30] Foreign Application Priority Data

Mar. 11, 1994 [DE] Germany .......................... 44 08 212.6

[51] Int. Cl.$^6$ ................................................. C07D 215/56
[52] U.S. Cl. .............................................................. 546/156
[58] Field of Search ............................................... 546/156

[56] References Cited

U.S. PATENT DOCUMENTS 5,140,033  8/1992  Schriewer et al. ...................... 514/312
5,252,734  10/1993  Schriewer et al. ......................... 544/64

FOREIGN PATENT DOCUMENTS 0287951  10/1988  European Pat. Off. .
0319906  6/1989  European Pat. Off. .
0387802  9/1990  European Pat. Off. .
0391132  10/1990  European Pat. Off. .
3910663  10/1990  Germany .
8906649  7/1989  WIPO .
9221659  12/1992  WIPO .

*Primary Examiner*—Bernard Dentz
*Attorney, Agent, or Firm*—Sprung Horn Kramer & Woods

[57] ABSTRACT

The invention relates to new 5-vinyl- and 5-ethinylquinolone- and -naphthyridonecarboxylic acids, to processes for their preparation, and to antibacterial compositions and feed additives containing them.

3 Claims, No Drawings

5-VINYL- AND 5-ETHINYL-QUINOLONE- AND -NAPHTHYRIDONE-CARBOXYLIC ACIDS

This is a division of application Ser. No. 08/398,328, filed on Mar. 3, 1995 now U.S. Pat. No. 5,578,604.

The invention relates to new 5-vinyl- and 5-ethinylquinolone- and -naphthyridone-carboxylic acids, to processes for their preparation, and to antibacterial compositions and feed additives containing them.

It has already been disclosed that 5-alkyl-quinolonecarboxylic acids have a antibacterial activity: for example, 5-alkyl-quinolonecarboxylic acids have been described in DE 3 910 663, EP 319 906, EP 287 951 and WO 8 906 849.

It has now been found that the new compounds of the formula (I)

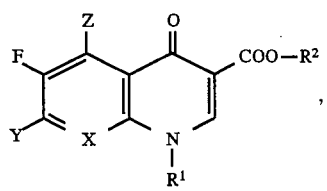

in which

R$^1$ represents straight-chain or branched C$_1$–C$_4$-alkyl which is optionally substituted by hydroxyl, halogen or C$_1$–C$_3$-alkoxy, or represents C$_3$–C$_6$-cycloalkyl which is optionally substituted by halogen or C$_1$–C$_3$-alkyl, or C$_2$–C$_4$-alkenyl, furthermore C$_1$–C$_3$-alkoxy, amino, monoalkylamino having 1 to 3 C atoms, dialkylamino having 2 to 6 C atoms, or phenyl which is optionally mono- to trisubstituted by halogen, R$^2$ represents hydrogen, alkyl having 1 to 4 carbon atoms or (5-methyl-2-oxo-1,3-dioxol-4-yl)-methyl, X represents a group CH, C-halogen, COCH$_3$, COCHF$_2$, C—CH$_3$ or N, Z represents $$-\underset{R^4}{\underset{|}{C}}=CH-R^3$$

or —C≡C—R$^5$, in which

R$^3$ represents hydrogen, C$_1$–C$_3$-alkyl, C$_1$–C$_3$-alkoxy or alkoxymethyl having 1 to 3 C atoms in the alkoxy moiety, R$^4$ represents hydrogen or halogen and R$^5$ represents hydrogen, C$_1$–C$_6$-alkyl which is optionally mono- to trisubstituted by halogen or hydroxyl, or C$_2$–C$_3$-alkenyl, alkoxy having 1 to 3 C atoms, alkoxymethyl having 1 to 3 C atoms in the alkoxy moiety, halogen or trimethylsilyl and Y represents

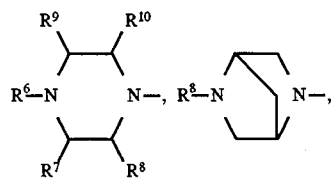

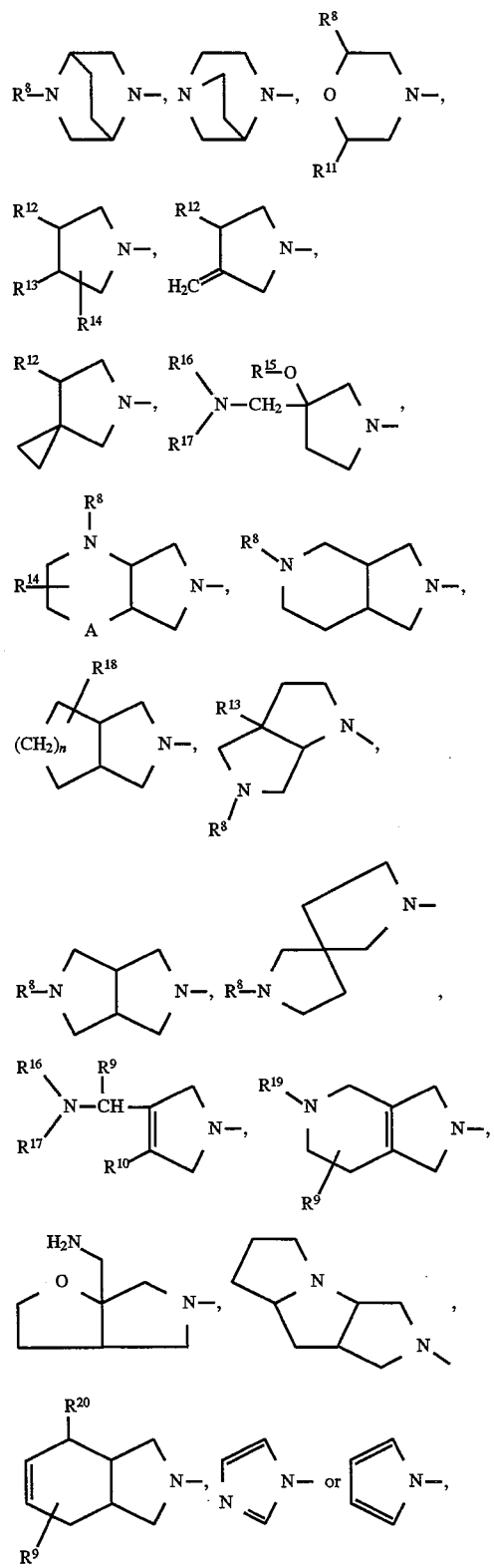

in which

R$^6$ represents hydrogen, straight-chain or branched C$_1$–C$_4$-alkyl which is optionally substituted by hydroxyl or methoxy, or cyclopropyl, oxoalkyl having 1 to 4 C atoms, or acyl having 1 to 3 C atoms, $R^7$ represents hydrogen, methyl, phenyl, thienyl or pyridyl,
$R^8$ represents hydrogen or methyl,
$R^9$ represents hydrogen or methyl,
$R^{10}$ represents hydrogen or methyl,
$R^{11}$ represents hydrogen, methyl or

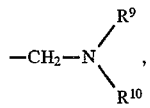

$R^{12}$ represents hydrogen, methyl, amino, alkyl- or dialkylamino which has 1 or 2 C atoms in the alkyl moiety and is optionally substituted by hydroxyl, or aminomethyl, alkyl- or dialkylaminomethyl which has 1 or 2 C atoms in the alkyl moiety and is optionally substituted by hydroxyl, or 1-imidazolyl,
$R^{13}$ represents hydrogen, hydroxyl, methoxy, methylthio or halogen, methyl, hydroxymethyl,
$R^{14}$ represents hydrogen or methyl,
$R^{15}$ represents hydrogen, methyl or ethyl,
$R^{16}$ represents hydrogen, methyl or ethyl,
$R^{17}$ represents hydrogen, methyl or ethyl,
$R^{18}$ represents hydroxyl,

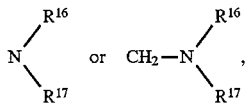

$R^{19}$ represents hydrogen, $C_1$–$C_3$-alkyl which is optionally substituted by hydroxyl, alkoxycarbonyl having 1 to 4 carbon atoms in the alkoxy moiety or $C_1$–$C_3$-acyl,
$R^{20}$ represents hydrogen, hydroxyl,

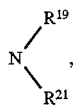

hydroxymethyl or

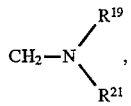

in which
$R^{21}$ denotes hydrogen or methyl,
A represents $CH_2$, O or a direct bond and
n represents 1 or 2,
and their pharmaceutically acceptable hydrates and acid addition salts and the alkali metal salts, alkaline earth metal salts, silver salts and guanidinium salts of the carboxylic acids on which these compounds are based have a powerful antibacterial activity.

They are therefore suitable as active compounds for use in human and veterinary medicine, veterinary medicine also including the treatment of fish by way of therapy or prevention of bacterial infections.

Preferred compounds of the formula (I) are those in which
$R^1$ represents optionally hydroxyl- or halogen-substituted $C_1$–$C_2$-alkyl, $C_3$–$C_5$-cycloalkyl, vinyl, amino, monoalkylamino having 1 to 2 C atoms, dialkylamino having 2 to 4 C atoms, or phenyl which is optionally mono- or disubstituted by halogen,
$R^2$ represents hydrogen, alkyl having 1 to 3 carbon atoms or (5-methyl-2-oxo-1,3-dioxol-4-yl)-methyl,
X represents a group CH, CF, CCl, $COCH_3$ or N,
Z represents

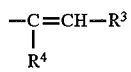

or $—C\equiv C—R^5$, in which
$R^3$ denotes hydrogen, $C_1$–$C_2$-alkyl, methoxy or methoxymethyl,
$R_4$ denotes hydrogen and
$R_5$ denotes hydrogen, $C_1$–$C_4$-alkyl which is optionally mono- to trisubstituted by fluorine, or $C_2$–$C_3$-alkenyl, methoxy or trimethylsilyl and
Y represents

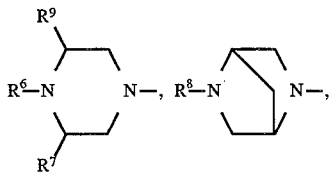

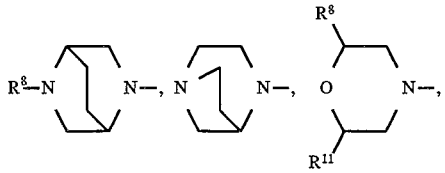

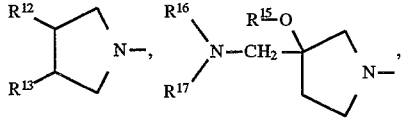

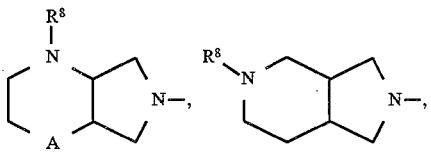

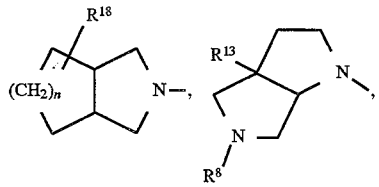

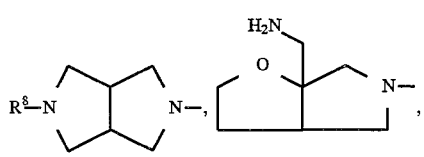

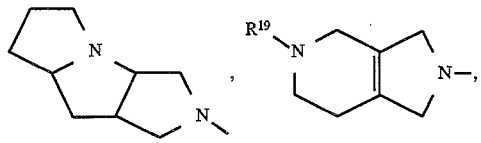

-continued

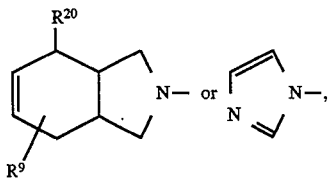

in which

R⁶ represents hydrogen, straight-chain or branched $C_1$–$C_3$-alkyl which is optionally substituted by hydroxyl, or oxoalkyl having 1 to 4 C atoms, R⁷ represents hydrogen, methyl or phenyl, R⁸ represents hydrogen or methyl, R⁹ represents hydrogen or methyl, R¹¹ represents hydrogen, methyl or —CH₂—NH₂, R¹² represents hydrogen, methyl, amino, methylamino, dimethylamino, aminomethyl, methylaminomethyl or ethylaminomethyl, R¹³ represents hydrogen, hydroxyl, methoxy, fluorine, methyl or hydroxymethyl, R¹⁵ represents hydrogen or methyl, R¹⁶ represents hydrogen or methyl, R¹⁷ represents hydrogen or methyl, R¹⁸ represents

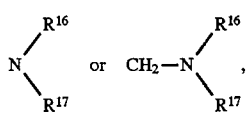

R¹⁹ represents hydrogen, methyl or ethyl,

R²⁰ represents

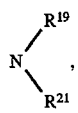

in which

R²¹ denotes hydrogen or methyl,

A represents CH₂, O or a direct bond and n represents 1 or 2.

Particularly preferred compounds of the formula (I) are those in which

R¹ represents methyl, ethyl, cyclopropyl, fluorocyclopropyl or phenyl which is optionally mono- or disubstituted by fluorine, R² represents hydrogen, methyl or ethyl, X represents a group CH, CF or CCl, Z represents —CH=CH₂ or —C≡C—R⁵, in which
R⁵ denotes hydrogen or trimethylsilyl and Y represents

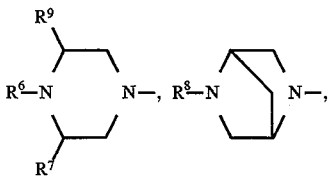

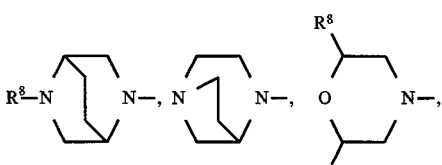

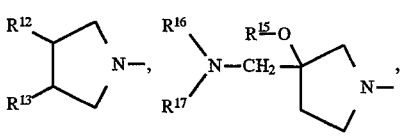

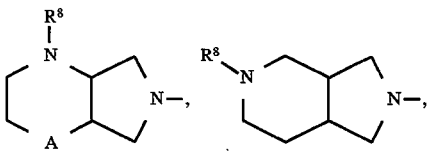

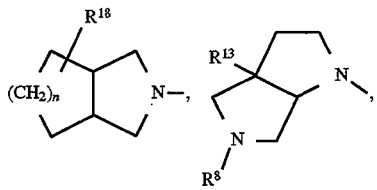

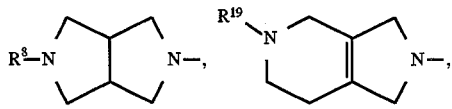

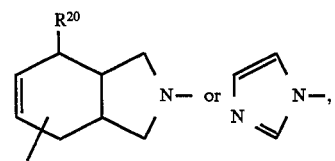

in which

R₆ represents hydrogen, methyl or ethyl which is optionally substituted by hydroxyl, R⁷ represents hydrogen or methyl, R⁸ represents hydrogen or methyl, R⁹ represents hydrogen or methyl, R¹¹ represents hydrogen or —CH₂—NH₂, R¹² represents hydrogen, methyl, amino, methylamino, aminomethyl or ethylaminomethyl, R¹³ represents hydrogen, hydroxyl or methoxy, R¹⁵ represents hydrogen or methyl, R¹⁶ represents hydrogen or methyl, R¹⁷ represents hydrogen or methyl, $R^{18}$ represents

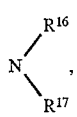

$R^{19}$ represents hydrogen or methyl,
$R^{20}$ represents

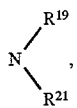

in which $R^{21}$ denotes hydrogen or methyl,

A represents $CH_2$, O or a direct bond and n represents 1.

Furthermore, it has been found that the compounds of the formula (I) are obtained when a compound of the formula (II)

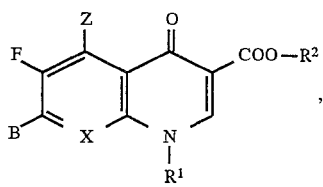

(II)

in which $R^1$, $R^2$, X and Z have the abovementioned meanings and

B represents halogen, in particular fluorine or chlorine, is reacted with compounds of the formula (III)

Y—H, (III)

in which

Y has the abovementioned meaning, if appropriate in the presence of acid scavengers.

If, for example, 1-cyclopropyl-5-vinyl-6,7,8-trifluoro-1,4-dihydro-4-oxo-3-quinolinecarboxylic acid and 1-methylpiperazine are used as starting compounds, the course of the reaction can be represented by the following equation:

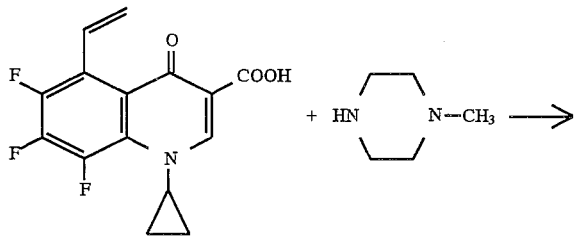

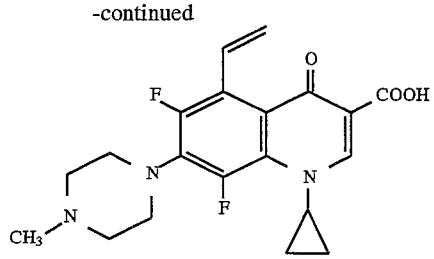

Furthermore, it has been found that compounds of the formula (I) are obtained when a compound of the formula (IV)

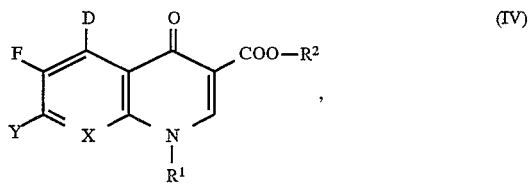

(IV)

in which $R^1$, $R^2$, X and Y have the abovementioned meanings and

D represents halogen, in particular chlorine, bromine or iodine, or a group $OSO_2R_F$, in which $R_F$ represents a perfluoroalkyl radical having 1 to 8 C atoms, is reacted with organometallic vinyl or alkinyl compounds of the formula (V)

M—Z, (V)

in which

Z has the abovementioned meaning and

M represents $SnR'_3$, $ZnX'$ or $B(OR'')_2$, in which
  R' denotes $C_1$–$C_4$-alkyl,
  R" denotes hydrogen or $C_1$–$C_4$-alkyl and
  X' denotes bromine or chlorine, in the presence of transition metal catalysts and, if appropriate, any existing protective groups are eliminated.

If, for example, 5-bromo-1-cyclopropyl-6,8-difluoro-1,4-dihydro-7-(4-methyl-1,4-piperazin-1-yl)-4-oxo-3-quinolinecarboxylic acid and tributylstannyl-trimethylsilyl-acetylene are used as starting compounds, the course of the reaction can be represented by the following equation:

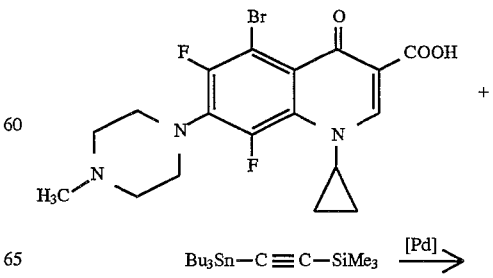

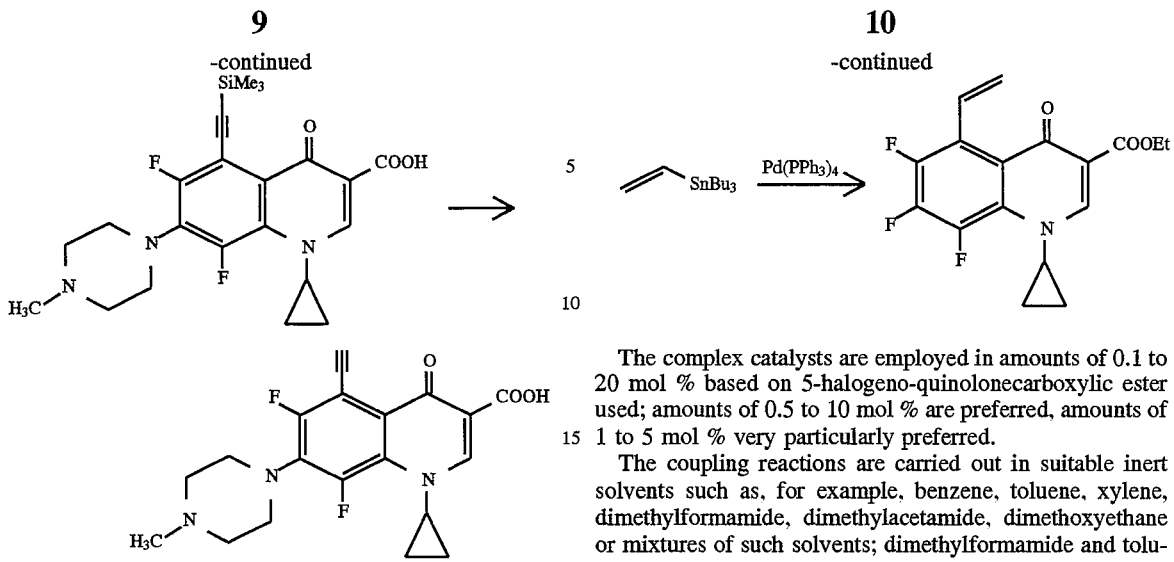

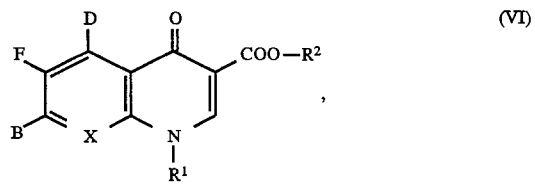

The compounds of the formula (II), which are used as starting compounds, are new. They can be prepared by reacting quinolinecarboxylic acid derivatives of the formula (VI)

in which

R¹, R², X and B have the abovementioned meanings and

D represents halogen, in particular iodine, bromine or chlorine, or a group $OSO_2R_F$ in which $R_F$ represents a perfluoroalkyl radical having 1 to 8 C atoms, with organometallic vinyl or alkinyl compounds of the formula (V)

M—Z, (V)

in which

M and Z have the abovementioned meanings, in the presence of transition metal catalysts and eliminating, if appropriate, any existing protective groups.

If, for example, vinyltributyltin and ethyl 5-bromo-1-cyclopropyl-6,7,8-trifluoro-1,4-dihydro-4-oxo-3-quinolinecarboxylates are used as starting compounds, the course of the reaction can be represented by the following equation:

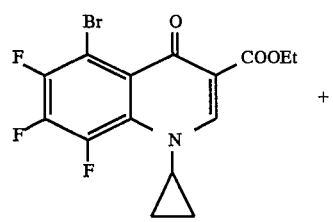

The complex catalysts are employed in amounts of 0.1 to 20 mol % based on 5-halogeno-quinolonecarboxylic ester used; amounts of 0.5 to 10 mol % are preferred, amounts of 1 to 5 mol % very particularly preferred.

The coupling reactions are carried out in suitable inert solvents such as, for example, benzene, toluene, xylene, dimethylformamide, dimethylacetamide, dimethoxyethane or mixtures of such solvents; dimethylformamide and toluene are preferred. Prior to use, the solvents are dried and freed from air by known processes.

The coupling reactions are carried-out at temperatures between 20° and 200° C.; temperatures between 50° and 180° C. are preferred.

The reaction time depends on the reactivity of the educts and is, in general, between 2 and 40 hours; reaction times between 4 and 24 hours are preferred.

The reactions are carried out under a protective gas atmosphere. Suitable protective gases are inert gases, such as, for example, helium, argon or nitrogen; nitrogen is preferred. In general, the coupling reaction is carried out under atmospheric pressure. Of course, it is also possible to carry out the reaction under reduced or elevated pressure.

The organometallic vinyl and alkinyl compounds required for the coupling reaction are either known or can be synthesized by methods known from the literature. Vinyltrialkyltin compounds, for example, can be prepared from the corresponding vinyl iodides, vinyl bromides or vinyl chlorides by obtaining the vinyl Grignard compounds by reaction with magnesium and reacting these vinyl Grignard compounds with a trialkyltin chloride to give the desired vinyltin derivatives.

Organometallic alkinyl compounds can be synthesized in the known manner, for example by metallating the 1-alkine with n-butyl-, sec-butyl- or tert-butyl-lithium at temperatures between −20° and −78° C. in an aprotic solvent such as, for example, tetrahydrofuran and subsequently reacting the product with a metal-halogen compound, such as, for example, zinc chloride, magnesium bromide, copper iodide or trialkyltin chloride. It is preferred to carry out the reaction at −78° C. Solvents other than tetrahydrofuran, which is preferred, include other ethers, such as diethyl ether, dipropyl ether or tert-butyl methyl ether, or mixtures of such ethers with aprotic aliphatic or aromatic solvents, such as n-hexane or toluene. In the case of both the vinyl and the alkinyl derivatives, the zinc chloride and trialkyltin derivatives are preferred. "Alkyl" in the case of the trialkyltin compounds is understood as meaning $C_1$- to $C_6$-alkyl; methyl and n-butyl are preferred.

Trialkylvinyltin compounds can also be obtained by methods known from the literature by hydrostannylation of alkines with trialkyltin hydrides in the presence of transition metal catalysts.

The organometallic vinyl and alkinyl compounds are reacted with 5-halogeno-quinolonecarboxylic acid derivatives of the general formula (IV) in the presence of a suitable catalyst by processes known in principle. "Halogen" represents iodine, bromine or chlorine; bromine and chlorine are preferred, bromine is particularly preferred.

Catalysts which are suitable are, for example, transition metal compounds of the metals cobalt, ruthenium, rhodium, iridium, nickel, palladium or platinum. Compounds of the metals platinum, palladium and nickel are preferred, palladium is particularly preferred. Such transition metals can be employed in the form of their salts, such as, for example, $NiCl_2$, $PdC_2$ or $Pd(OAc)_2$, or in the form of complexes with suitable ligands. The use of complexes is preferred. Ligands which are preferably employed are phosphines, such as, for example, triphenylphosphine, tri(o-tolyl)phosphine, trimethylphosphine, tributylphosphine and tri(2-furyl) phosphine, triphenylphosphine is preferred. Preferred complex catalysts which may be mentioned are bis(triphenylphosphine)nickel(II) chloride, bis(triphenylphosphine)palladium(II) chloride, tris(triphenylphosphine)palladium(0) and tetrakis(triphenylphosphine)palladium(0).

The compounds of the formula (IV), which are used as starting compounds, are known or can be prepared by known processes.

Most of the amines of the formula (III), which are used as starting compounds, are known. Chiral amines can be employed both in the form of racemates and as enantiomerically or diastereomerically pure compounds. Examples which may be mentioned are:

Piperazine,
1-Methylpiperazine,
1-Ethylpiperazine,
1-(2-Hydroxyethyl)-piperazine,
3-Methylpiperazine,
cis-2,6-Dimethyl-piperazine,
cis-2,3-Dimethyl-piperazine,
1,2-Dimethylpiperazine,
1-Cyclopropyl-piperazine,
2-Phenyl-piperazine,
2-(4-Pyridyl)-piperazine,
2-(2-Thienyl)-piperazine,
1,4-Diazabicyclo[3.2.1]octane,
8-Methyl-3,8-diazabicyclo[3.2.1]octane dihydrochloride,
3-Methyl-3,8-diazabicyclo[3.2.1]octane dihydrochloride,
2,5-Diazabicyclo[2.2.1]heptane dihydrochloride,
2-Methyl-2,5-diazabicyclo[2.2.1]heptane dihydrochloride,
2,5-Diazabicyclo[2.2.2]octane dihydrochloride,
2-Methyl-2,5-diazabicyclo[2.2.2]octane dihydrochloride,
1,4-Diazabicyclo[3.1.1]heptane,
Morpholine,
2,6-Dimethyl-morpholine,
2-Aminomethyl-morpholine,
2-tert-Butoxycarbonylaminomethyl-morpholine,
2-Methylaminomethyl-morpholine,
2-Dimethylaminomethyl-morpholine,
Imidazole,
4-Methyl-imidazole,
Pyrrole,
3-Aminomethyl-2,5-dihydro-pyrrole,
3-Aminomethyl-4-methyl-2,5-dihydro-pyrrole,
3-(1-Aminoethyl)-2,5-dihydro-pyrrole,
3-Amino-azetidine,
3-tert-Butoxycarbonylamino-azetidine,
3-tert-Butoxycarbonylamino-2-methyl-azetidine,
3-tert-Butoxycarbonylamino-3-methyl-azetidine,
3-tert-Butoxycarbonylaminomethyl-azetidine,
Pyrrolidine,
3-Amino-pyrrolidine,
3-tert-Butoxycarbonylamino-pyrrolidine,
3-(2,2-Dimethyl-propylidenamino)-pyrrolidine,
3-Methylamino-pyrrolidine,
3-Dimethylamino-pyrrolidine,
3-Aminomethyl-pyrrolidine,
3-tert-Butoxycarbonylaminomethyl-pyrrolidine,
4-Chloro-3-tert-butoxycarbonylaminomethyl-pyrrolidine,
3-tert-Butoxycarbonylaminomethyl-3-methyl-pyrrolidine,
3-tert-Butoxycarbonylamino-4-methyl-pyrrolidine,
3-tert-Butoxycarbonylaminomethyl-3-methoxy-pyrrolidine,
3-Methylaminomethyl-pyrrolidine,
3-Ethylaminomethyl-pyrrolidine,
4-tert-Butoxycarbonylamino-2-methyl-pyrrolidine,
2-Methyl-3-methylamino-pyrrolidine,
2-Methyl-4-methylamino-pyrrolidine,
3-(2-Hydroxyethylamino)-pyrrolidine,
3-Hydroxy-pyrrolidine,
3-Hydroxymethyl-pyrrolidine,
4-Amino-3-hydroxy-pyrrolidine,
3-Hydroxy-4-methylamino-pyrrolidine,
3-tert-Butoxycarbonylamino-4-methoxy-pyrrolidine,
3-Methylaminomethyl-3-hydroxy-pyrrolidine,
3-Dimethylaminomethyl-3-hydroxy-pyrrolidine,
3-Diethylaminomethyl-3-hydroxy-pyrrolidine,
3-tert-Butylaminomethyl-3-hydroxy-pyrrolidine,
3-Methylamino-4-hydroxymethyl-pyrrolidine,
4-Methoxy-3-methylamino-pyrrolidine,
3-Methoxy-3-methylaminomethyl-pyrrolidine,
3-Amino-4-methoxy-2-methyl-pyrrolidine,
3-tert-Butoxycarbonylamino-3-methyl-pyrrolidine,
3-Methyl-4-tert-butoxycarbonylaminomethyl-pyrrolidine,
3-Methoxy-4-tert-butoxycarbonylaminomethyl-pyrrolidine,
3-(1-Imidazolyl)-pyrrolidine,
6-Hydroxy-3-azabicyclo[3.3.0]octane,
6-Amino-3-azabicyclo[3.3.0]octane,
1-Amino-3-azabicyclo[3.3.0]octane,
1-Aminomethyl-3-azabicyclo[3.3.0]octane,
1-Ethylaminomethyl-3-azabicyclo[3.3.0]octane,
6-Amino-3-azabicyclo[4.3.0]nonane,
3-Amino-4-methylene-pyrrolidine,
7-Amino-5-azaspiro[2.4]heptane,
3,7-Diazabicyclo[3.3.0]octane,
3-Methyl-3,7-diazabicyclo[3.3.0]octane,
2,8-Diazabicyclo[4.3.0]nonane,
2-Methyl-2,8-diazabicyclo[4.3.0]nonane,
3-Methyl-3,8-diazabicyclo[4.3.0]nonane,
2-Oxa-5,8-diazabicyclo[4.3.0]nonane,
5-Methyl-2-oxa-5,8-diazabicyclo[4.3.0]nonane,
2,7-Diazablcyclo[3.3.0]octane,
2-Methyl-2,7-diazabicyclo[3.3.0]octane,
3-Methyl-2,7-diazabicyclo[3.3.0]octane,
4-Methyl-2,7-diazabicyclo[3.3.0]octane,
tert-Butyl 5-methyl-2,7-diazabicyclo[3.3.0]octane-7-carboxylate,
7-Methyl-2,7-diazabicyclo[3.3.0]octane,
8-Methyl-2,7-diazabicyclo[3.3.0]octane,
7,8-Dimethyl-2,7-diazabicyclo[3.3.0]octane,
2,3-Dimethyl-2,7-diazabicyclo[3.3.0]octane,
2,8-Dimethyl-2,7-diazabicyclo[3.3.0]octane,
1,4-Diazatricyclo[6.2.0.0$^{2,6}$]decane,
1,4-Diazatricyclo[6.3.0.0$^{2,6}$]undecane,
2,7-Diazaspiro[4.4]nonane,
2-Methyl-2,7-diazaspiro[4.4]nonane,
4-Amino-1,3,3a,4,7,7a-hexahydroisoindole,
4-Methylamino-1,3,3a,4,7,7a-hexahydroisoindole,
5-Methyl-4-methylamino-1,3,3a,4,7,7a-hexahydroisoindole,
6-Methyl-4-methylamino-1,3,3a,4,7,7a-hexahydroisoindole, 7-Methyl-4-methylamino-1,3,3a,4,7,7a-hexahydroisoindole,
7a-Methyl-4-methylamino-1,3,3a,4,7,7a-hexahydroisoindole,
6,7-Dimethyl-4-methylamino-1,3,3a,4,7,7a-hexahydroisoindole,
4-Dimethylamino-1,3,3a-4,7,7a-hexahydroisoindole,
4-Ethylamino-1,3,3a,4,7,7a-hexahydroisoindole,
4-Aminomethyl-1,3,3a,4,7,7a-hexahydroisoindole,
4-Methylaminomethyl-1,3,3a,4,7,7a-hexahydroisoindole,
4-Hydroxy-1,3,3a,4,7,7a-hexahydroisoindole,
2,3,4,5,6,7-Hexahydro-1H-pyrrolo[3,4-c]pyridine,
5-Methyl-2,3,4,5,6,7-hexahydro-1H-pyrrolo[3,4-c]pyridine,
5-Ethyl-2,3,4,5,6,7-hexahydro-1H-pyrrolo[3,4-c]pyridine,
5-(tert-Butoxycarbonyl)-2,3,4,5,6,7-hexahydro-1H-pyrrolo[3,4-c]pyridine.

The reaction of (II) with (III), in which the compounds (III) can also be employed in the form of their salts, such as, for example, hyarochlorides, is preferably carried out in a diluent, such as dimethyl sulphoxide, N,N-dimethylformamide, N-methylpyrrolidone, hexamethylphosphoric triamide, sulpholane, acetonitrile, water, an alcohol, such as methanol, ethanol, n-propanol, isopropanol, glycol monomethyl ether, or pyridine. Mixtures of these diluents can also be used.

Acid binders which can be used are all customary inorganic and oganic acid-binding agents. These preferably include the alkali metal hydroxides, alkali metal carbonates, organic amines and amidines. Particularly suitable individual substances which may be mentioned are: triethylamine, 1,4-diazabicyclo[2.2.21]octane (DABCO), 1,8-diazabicyclo[5.4.0]undec-7-ene (DBU), or excess amine (III).

The reaction temperatures can be varied within a substantial range. In general, the process is carried out between approximately 20° and 200° C., preferably between 80° and 180° C.

The reaction can be carried out under atmospheric pressure, but also under elevated pressure. In general, pressures between approximately 1and 100 bar, preferably between 1 and 10 bar, are used.

When carrying out the process according to the invention, 1 to 15 mol, preferably 1 to 6 mol, of the compound (III) are employed per mol of the compound (II).

Free amino groups can be protected during the reaction by a suitable amino protective group, for example by the tert-butoxycarbonyl radical, and again set free after the reaction has ended by treatment with a suitable acid, such as hydrochloric acid or trifluoroacetic acid.

The esters according to the invention are obtained reacting an alkali metal salt of the basic carboxylic acid, which can optionally be protected on the N atom by a protective group, such as the tert-butoxycarbonyl radical, with suitable halogenoalkyl derivatives in a solvent such as dimethylformamide, dimethylacetamide, N-methylpyrrolidone, dimethyl sulphoxide or tetramethylurea, at temperatures from approximately 0° to 100° C., preferably 0° to 50° C.

The acid addition salts of the compounds according to the invention are prepared in the customary manner for example by dissolving the betains in a sufficient amount of aqueous acid and precipitating the salt with an organic solvent which is miscible with water, such as methanol, ethanol, acetone or acetonitrile. It is also possible to heat equivalent amounts of betaine and acid in water or an alcohol, such as glycol monomethyl ether, and subsequently evaporating the mixture to dryness or filtering off the precipitated salt by suction. Pharmaceutically acceptable salts are, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal salts or alkaline earth metal salts of the carboxylic acids according to the invention are obtained, for example, by dissolving the betaine in a substoichiometric amount of alkali metal hydroxide solution or alkaline earth metal hydroxide solution, removing undissolved betaine by filtration and evaporating the filtrate to dryness. Pharmaceutically acceptable salts are sodium salts, potassium salts or calcium salts. The corresponding silver salts are obtained by reacting an alkali metal salt or alkaline earth metal salt with a suitable silver salt, such as silver nitrate.

The active compounds listed in the table which follows can be prepared additionally to the active compounds mentioned in the examples:

| $R^1$ | $R^2$ | X | Z | Y |
|---|---|---|---|---|
| cyclopropyl | H | CF | $-CH=CH_2$ | piperazinyl (HN, N–) |
| cyclopropyl | H | CF | $-CH=CH_2$ | 2-methylpiperazinyl (HN, N–, Me) |

-continued

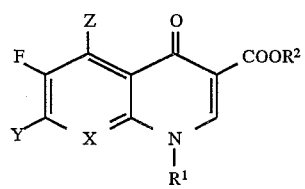

| R¹ | R² | X | Z | Y |
|---|---|---|---|---|
| cPr | H | CF | —CH=CH₂ | 2,6-dimethylpiperazin-1-yl |
| cPr | H | CF | —CH=CH₂ | 1,4-diazabicyclic N |
| cPr | H | CF | —CH=CH₂ | 3,8-diazabicyclic (HN) |
| cPr | H | CF | —CH=CH₂ | 3-(methylamino)pyrrolidin-1-yl |
| cPr | H | CF | —CH=CH₂ | 3-(aminomethyl)pyrrolidin-1-yl |
| cPr | H | CF | —CH=CH₂ | 3-amino-4-methylpyrrolidin-1-yl |
| cPr | H | CF | —CH=CH₂ | 3-amino-4-methylenepyrrolidin-1-yl |
| cPr | H | CF | —CH=CH₂ | 3-(methylamino)-4-methylenepyrrolidin-1-yl |
| cPr | H | CF | —CH=CH₂ | octahydropyrrolo[3,4-b]pyrrol-yl |
| cPr | H | CF | —CH=CH₂ | 4-amino-7-methyl-2,3,3a,4,7,7a-hexahydro-1H-isoindol-2-yl |

-continued

|   |   |   |   |   |
|---|---|---|---|---|
| R¹ | R² | X | Z | Y |
| cyclopropyl | H | CF | —CH=CH₂ | MeNH₂-substituted hexahydroisoindolin-N-yl |
| cyclopropyl | H | CF | —CH=CH₂ | octahydropyrrolo[3,4-b][1,4]oxazin-N-yl |
| 2,4-difluorophenyl | H | CF | —CH=CH₂ | 4-methylpiperazin-1-yl |
| 2,4-difluorophenyl | H | CF | —CH=CH₂ | piperazin-1-yl |
| 2,4-difluorophenyl | H | CF | —CH=CH₂ | 2-methylpiperazin-1-yl |
| 2,4-difluorophenyl | H | CF | —CH=CH₂ | 3-aminopyrrolidin-1-yl |
| 2,4-difluorophenyl | H | CF | —CH=CH₂ | 3-amino-4-methylpyrrolidin-1-yl |
| 2,4-difluorophenyl | H | CF | —CH=CH₂ | 3-amino-4-methylenepyrrolidin-1-yl |
| 2,4-difluorophenyl | H | CF | —CH=CH₂ | 4-aminohexahydroisoindolin-N-yl |

-continued

[Structure: bicyclic quinolone core with substituents F, Z, Y, X, N-R¹, and COOR² on carbonyl-containing ring]

| R¹ | R² | X | Z | Y |
|---|---|---|---|---|
| 2,4-difluorophenyl | H | CF | −CH=CH₂ | MeNH-substituted hexahydroisoindol-2-yl |
| cyclopropyl | H | CF | −C≡CH | piperazin-1-yl |
| cyclopropyl | H | CF | −C≡CH | 3-methylpiperazin-1-yl |
| cyclopropyl | H | CF | −C≡CH | 2,5-dimethylpiperazin-1-yl |
| cyclopropyl | H | CF | −C≡CH | 1,4-diazabicyclo[2.2.2]octan-1-yl |
| cyclopropyl | H | CF | −C≡CH | 2,5-diazabicyclic N-yl |
| cyclopropyl | H | CF | −C≡CH | 3-(methylamino)pyrrolidin-1-yl |
| cyclopropyl | H | CF | −C≡CH | 3-(aminomethyl)pyrrolidin-1-yl |
| cyclopropyl | H | CF | −C≡CH | 3-amino-4-methylenepyrrolidin-1-yl |
| cyclopropyl | H | CF | −C≡CH | (aminomethyl)-oxa-bicyclic pyrrolidin-N-yl |

-continued

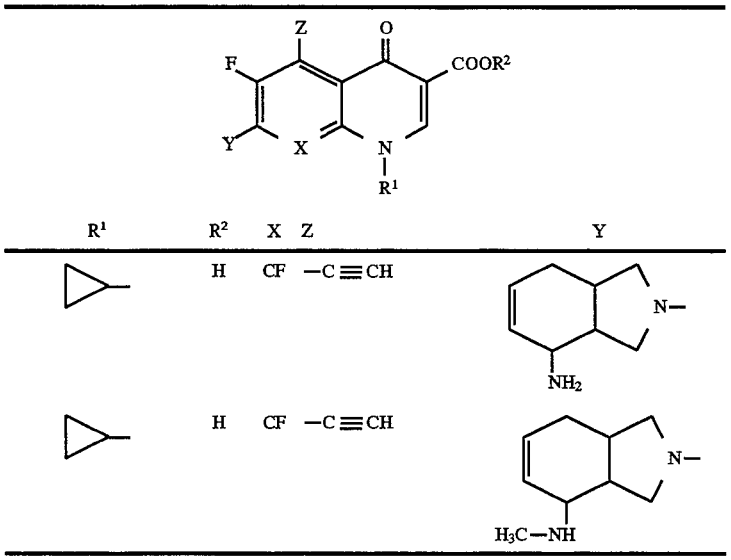

| R¹ | R² | X | Z | Y |
|---|---|---|---|---|
| ▷− | H | CF | −C≡CH | (cyclohexene fused ring with NH₂ and N−) |
| ▷− | H | CF | −C≡CH | (cyclohexene fused ring with H₃C−NH and N−) |

The compounds according to the invention have a powerful antibiotic activity and display a low toxicity combined with a broad antibacterial spectrum against Gram-positive and Gram-negative microorganisms, in particular against enterobacteria, especially also against those which are resistant to a range of antibiotics such as, for example, penicillins, cephalosporins, aminoglycosides, sulphonamides or tetracyclines.

These valuable properties allow them to be used as chemotherapeutic active compounds in medicine and as preservatives for inorganic and organic materials, in particular any type of organic material, for example polymers, lubricants, paints, fibres, leather, paper and wood, of foodstuffs and of water.

The compounds according to the invention are active against a very broad range of microorganisms. With their aid, Gram-negative and Gram-positive bacteria and bacteria-like microorganisms can be combated, and the diseases caused by these pathogens can be prevented, ameliorated and/or cured.

The compounds according to the invention are distinguished by a more powerful activity against dormant and resistant microorganisms. In the case of dormant bacteria, i.e. bacteria which show no detectable growth, the compounds act at concentrations far below the concentrations of previously known substances. This relates not only to the amount to be employed, but also to the speed of destruction. Such results were observed in Gram-positive and -negative bacteria, in particular in the case of *Staphylococcus aureus*, *Pseudomonas aeruginosa*, *Enterococcus faecalis* and *Escherichia coli*.

The compounds according to the invention also show surprisingly improved activity against bacteria which are classified as less sensitive to comparable substances, in particular resistant *Staphylococcus aureus*, *Escherichia coli*, *Pseudomonas aeruginosa* and *Enterococcus faecalis*.

Since the compounds according to the invention have a powerful activity against bacteria and bacteria-like microorganisms, they are very particularly suitable for the prophylaxis and chemotherapy of local and systemic infections in human and veterinary medicine which are caused by these pathogens.

The compounds according to the invention are particularly active against typical and atypical mycobacteria and *Helicobacter pylori*, and against bacteria-like microorganisms, such as, for example, mycoplasmas and rickettsias.

The compounds are furthermore suitable for combating protozoonoses and helminthoses.

The compounds according to the invention can be used in a range of pharmaceutical preparations. Preferred pharmaceutical preparations which my be mentioned are tablets, coated tablets, capsules, pills, granules, suppositories, solutions, suspensions and emulsions, pastes, ointments, gels, creams, lotions, powders and sprays.

The minimum inhibitory concentrations (MICs) were determined in serial dilution tests using Iso-Sensitest Agar (Oxoid). For each test substance, a series of agar plates was prepared which contained concentrations of the active compound which decreased as a result of dilution to twice the volume each time. The agar plates were inoculated using a Multipoint Inoculator (Denley). For inoculation, overnight cultures of the pathogens were used which had previously been diluted to such a concentration that each inoculation point contained approximately $10^4$ colony-forming particles. The inoculated agar plates were incubated at 37° C., and the microbial growth was determined after approximately 20 hours. The MIC value (µg/ml) indicates the lowest concentration of active compound at which no growth was discernible with the naked eye.

Table 2 shows the MIC values of some of the compounds according to the invention in comparison with Compound K (1-cyclopropyl-5-ethyl-6,8-difluoro-1,4-dihydro-7-(4-methyl-1-piperazinyl)-4-oxo-3-quinolinecarboxylic acid), which is known from EP 287 951, which values demonstrate that the compounds according to the invention have a better activity when compared with a similar quinolone carboxylic acid having a $C_2$ substituent in the 5-position.

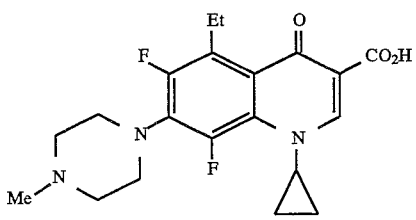

(K)

TABLE 2

| Test Strain | | K | 1 | 2 | 3 | 4 | 5 | 6 | 7 | 11 |
|---|---|---|---|---|---|---|---|---|---|---|
| | | | | | | MIC values Compound | | | | |
| E. coli | Neumann | 0.25 | 0.06 | 0.06 | ≦0.015 | ≦0.015 | 0.015 | 0.03 | 0.03 | |
| Enterobater | cloaceae 2427 | 1 | 0.25 | 0.125 | 0.06 | ≦0.015 | 0.125 | 0.125 | 0.125 | |
| | aer.ICB 5240 | ≦128 | 32 | 16 | 8 | 4 | 4 | 8 | 32 | |
| Staphylococcus aureus | ICB 25701 | 64 | 64 | 1 | 0.5 | 2 | 0.03 | 0.03 | 0.5 | |
| | ATTC 29213 | 8 | 0.25 | 0.06 | 0.03 | ≦0.015 | ≦0.015 | ≦0.015 | 0.015 | |
| | 133 | 16 | 0.25 | 0.06 | 0.03 | 0.03 | ≦0.015 | ≦0.015 | 0.015 | |
| Enterococcus faecalis | 27101 | 64 | 1 | 0.125 | 0.125 | 0.06 | 0.03 | 0.03 | 0.125 | |
| | 9790 | 64 | 1 | 0.125 | 0.125 | 0.125 | 0.03 | 0.03 | 0.125 | |

Table 3 lists MIC values of compounds according to the invention against microorganisms which aye specific to veterinary medicine. The comparison compound shown in this case is enrofloxacin (ENRO), which is a therapeutic used in veterinary medicine.

TABLE 3

| | Test strain | MIC values | | |
|---|---|---|---|---|
| | | | Compound | |
| | | ENRO | 5 | 6 |
| E. coli | G293 Lh | 32 | 32 | 8 |
| | 21 Bui | 32 | 16 | 4 |
| Staph. | Z433-4 LH | 0.25 | 0.03 | 0.015 |
| | Ky 469 We | 0.12 | 0.03 | 0.015 |
| | Z 318 Lh | 8 | 2 | 0.06 |

Preparation of intermediates

EXAMPLE A

Ethyl 1-cyclopropyl-6,7,8-trifluoro-1,4-dihydro-4-oxo-5-vinyl-3-quinolinecarboxylate 5.9 g of ethyl 5-bromo-1-cyclopropyl-6,7,8-trifluoro-1,4-dihydro-4-oxo-3-quinolinecarboxylate, 6.7 g of tributylvinylstannane and 0.69 g of tetrakis(triphenylphosphine) palladium(0) are refluxed for 10 hours in 60 ml of absolute toluene under a nitrogen atmosphere. The reaction mixture is cooled to −18° C., and the solid which has precipitated is filtered off with suction, washed with toluene and dried. 4.46 of the title compound are obtained (88% of theory).

Melting point: 188°–189° C.

EXAMPLE B

1-Cyclopropyl-6,7,8-trifluoro-1,4-dihydro-4-oxo-5-vinyl-3-quinolinecarboxylic acid 3 g of the product of Example A are refluxed for 1.5 hours in a mixture of 40 ml of glacial acetic acid, 2 ml of water and 0.6 ml of concentrated sulphuric acid. The reaction mixture is then treated with 40 ml of water and cooled to room temperature. The product is filtered off with suction, washed with water and dried. 2.08 g of the title compound are obtained (75% of theory).

Melting point: 215°–216° C.

EXAMPLE C

Ethyl 1-(2,4-difluorophenyl)-6,7,8-trifluoro-1,4-dihydro-4-oxo-5-vinyl-3-quinolinecarboxylate 4.6 g of ethyl 5-bromo-1-(2,4-difluorophenyl)-6,7,8-trifluoro-1,4-dihydro-4-oxo-3-quinolinecarboxylate, 4.5 g of tributylvinylstannane and 0.46 g of tetrakis (triphenylphosphine)palladium(0) are refluxed for 10 hours in 40 ml of absolute toluene under a nitrogen atmosphere. The product is filtered off with suction at room temperature, washed with water and dried. 2.7 g of the title compound are obtained (66% of theory).

Melting point: 174°–176° C.

EXAMPLE D 1-(2,4-Difluorophenyl)-6,7,8-trifluoro-1,4-dihydro-4-oxo-5-vinyl-3-quinolinecarboxylic acid 2 g of the product of Example C are refluxed for 2 hours in a mixture of 15ml of glacial acetic acid, 1.5 ml of water and 0.7 ml of concentrated sulphuric acid. The product is filtered off with suction at room temperature, washed with water and dried. 1.3 g of the title compound are obtained (71% of theory).

Melting point: 201°–202° C.

EXAMPLE E

Ethyl 1-cyclopropyl-6,7,8-trifluoro-1,4-dihydro-5-trimethylsilylethinyl-4-oxo-3-quinolinecarboxylate 1.95 g of ethyl 5-bromo-1-cyclopropyl-6,7,8-trifluoro-1,4-dihydro-4-oxo-3-quinolinecarboxylate, 2.7 g of tributylstannyl-trimethylsilyl-acetylene and 0.29 g of tetrakis-(triphenylphosphine)palladium(0) are refluxed for 4 hours in 20 ml of absolute toluene under a nitrogen atmosphere. The reaction mixture is filtered at room temperature; the solid is washed with a small amount of toluene and dried 1.6 g of the title compound are obtained (78% of theory).

Melting point: 267°–269° C.

EXAMPLE F

Ethyl 1-cyclopropyl-5-ethinyl-6,7,8-trifluoro-1,4-dihydro-4-oxo-3-quinolinecarboxylate 1 g of the product of Example E and 0.45 g of potassium fluoride are stirred for 1 hour at room temperature in a mixture of 20 ml of dimethylformamide, 10 ml of chloroform and 1 ml of water. After chloroform has been added, the organic phase is separated off, extracted by shaking with water, dried over sodium sulphate and concentrated. The residue is boiled briefly in 20 ml of methanol. When the mixture has cooled to 0° C., the solid obtained is filtered off with suction and dried. 0.63 g of the title compound is obtained (77% of theory).

Melting point: 190° C. (decomp.)

EXAMPLE G

Ethyl 1-cyclopropyl-6,8-difluoro-1,4-dihydro-7-(4-methyl-1-piperazinyl)-5-trimethylsilyl-4-oxo-3-quinolinecarboxylate 1.1 g of ethyl 5-bromo-1-cyclopropyl-6,8-difluoro-1,4-dihydro-7-(4-methyl-1-piperazinyl)-4-oxo-3-quinolinecarboxylate, 1.2 g of tributylstannyl-trimethylsilylacetylene and 0.135 g of tetrakis (triphenylphosphine)palladium(0) are refluxed for 3 hours in 10 ml of absolute toluene. The reaction mixture is treated with a further 5 ml of toluene and filtered while hot. The product crystallizes out of the filtrate. After filtration with suction and drying, 0.63 g of the title compound is obtained (56% of theory).

Melting point: 231°–233° C.

Preparation of the active confounds

EXAMPLE 1

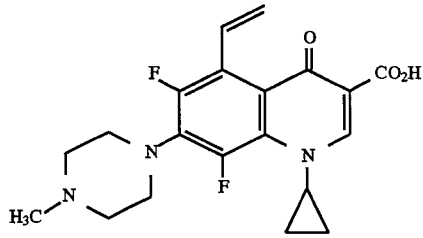

1.55 g (5 mmol) of 1-cyclopropyl-6,7,8-trifluoro-1,4-dihydro-4-oxo-5-vinyl-3-quinolinecarboxylic acid are refluxed for 1 hour in a mixture of 10 ml of acetonitrile and 5 ml of dimethylformamide together with 0.55 g (5 mol) of 1,4-diazabicyclo[2.2.2]octane and 0.75 g (7.5 mmol) of N-methylpiperazine. The mixture is concentrated, the residue is stirred with water, and the undissolved precipitate is filtered off with suction, washed with water and acetonitrile, and dried at 100° C. under high vacuum.

Yield: 1.0 g (51% of theory) of 1-cyclopropyl-6,8-difluoro-1,4-dihydro-4-oxo-7-(4-methyl-1-piperazinyl)-4-oxo-5-vinyl-3-quinolinecarboxylic acid.

Melting point: 242°–245° C. (with decomposition).

EXAMPLE 2

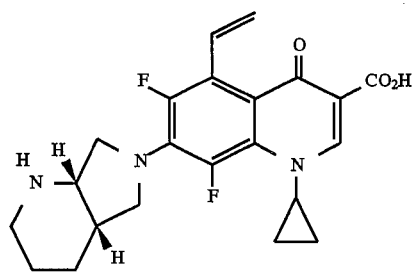

The reaction is carried out analogously to Example 1 using cis-2,8-diazabicyclo[4.3.0]nonane to give 1-cyclopropyl-7-(cis-2,8-diazabicyclo[4.3.0]non-8-yl)-6,8-difluoro-1,4-dihydro-4-oxo-5-vinyl-3-quinolinecarboxylic acid of melting point 217°–219° C. (with decomposition) (from glycol monomethyl ether).

EXAMPLE 3

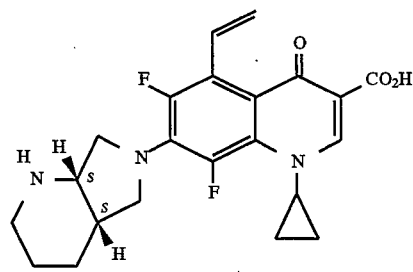

0.93 g of 1-cyclopropyl-6,7,8-trifluoro-1,4-dihydro-4-oxo-5-vinyl-3-quinolinecarboxylic acid, 0.57 g of S,S-2,8-diazabicyclo[4.3.0]nonane and 0.34 g of DABCO are refluxed for 2 hours in a mixture of 6 ml of acetonitrile and 3 ml of dimethylformamide. The reaction mixture is concentrated in vacuo, and the residue is boiled up in 10 ml of water. The product is filtered off with suction while hot, washed with water and dried. 0.76 g of 1-cyclopropyl-7-(S,S-2,8-diazabicyclo[4.3.0]non-8-yl)-6,8-difluoro-1,4-dihydro-4-oxo-5-vinyl-3-quinolinecarboxylic acid is obtained.

Melting point: 195°–197° C. (with decomposition).

EXAMPLE 4

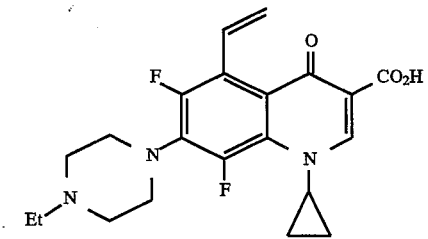

0.93 g of 1-cyclopropyl-6,7,8-trifluoro-1,4-dihydro-4-oxo-5-vinyl-3-quinolinecarboxylic acid, 0.51 g of 4-ethyl-1,4-piperazine and 0.34 g of DABCO are refluxed for 2.5 hours in a mixture of 6 ml of acetonitrile and 3 ml of dimethylformamide. At room temperature, the reaction mixture is treated with 15 ml of water, and the product is filtered off with suction, washed with water and dried. 0.79 g of 1-cyclopropyl-7-(4-ethyl-1-piperazinyl)-6,8-difluoro-1,4-dihydro-4-oxo-5-vinyl-3-quinolinecarboxylic acid is obtained.

Melting point: 198°–200° C.

EXAMPLE 5

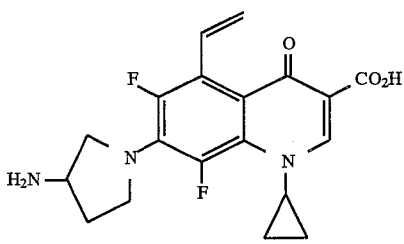

A) A solution of 0.39% of 3-amino-pyrrolidine in 4 ml of acetonitrile is treated with a solution of 0.75 g of 3-nitrobenzaldehyde in 4 ml of acetonitrile. After 1 hour at room temperature, the reaction mixture is treated with a solution of 1 g of DABCO and 0.93 g of 1-cyclopropyl-6,7,8-trifluoro-1,4-dihydro-4-oxo-5-vinyl-3-quinolinecarboxylic acid in 4 ml of dimethylformamide. After 1 hour under reflux, the reaction mixture is cooled to 0° C. and the product is filtered off with suction and dried. 1.33 g of 1-cyclopropyl-6,8-difluoro-1,4-dihydro-7-(3-(3-nitro-benzylideneamino)-pyrrolidin-1-yl)-4-oxo-5-vinyl-3-quinolinecarboxylic acid are obtained.

Melting point: 193°–195° C. (with decomposition).

B) 1 g of the product of Part A) of the protocol is refluxed for 1.5 hours in a mixture of 22 ml of methylene chloride and 30 ml of 3N aqueous hydrochloric acid. After the product had cooled to 0° C., it was filtered off with suction, washed with acetonitrile and dried. 0.66 g of 7-(3-aminopyrrolidin-1-yl)-1-cyclopropyl-6,8-difluoro-1,4-dihydro-4-oxo-5-vinyl-3-quinolinecarboxylic acid hydrochloride is obtained.

Melting point: >300° C.

EXAMPLE 6

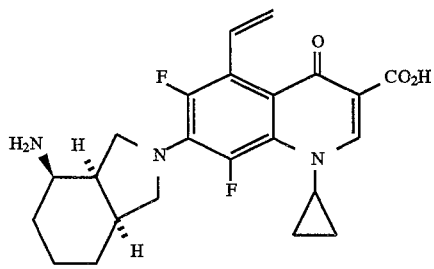

0.93 g of 1-cyclopropyl-6,7,8-trifluoro-1,4-dihydro-4-oxo-5-vinyl-3-quinolinecarboxylic acid, 0.62 g of 4-amino-1,3,3a,4,7,7a-hexahydro-isoindole and 0.34 g of DABCO are refluxed for 1 hour in a mixture of 6 ml of acetonitrile and 3 ml of dimethylformamide. The reaction mixture is treated with 20 ml of water, and the product is filtered off with suction, washed with water and dried. 1 g of 7-(4-amino-1,3,3a,4,7,7a-hexahydro-isoindol-2-yl)-1-cyclopropyl-6,8-difluoro-1,4-dihydro-4-oxo-5-vinyl-3-quinolinecarboxylic acid is obtained.

Melting point: 224°–227° C. (with decomposition)

EXAMPLE 7

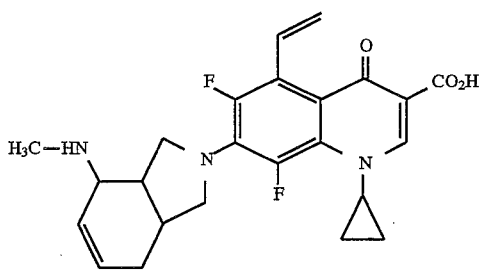

0.46 g of 1-cyclopropyl-6,7,8-trifluoro-1,4-dihydro-4-oxo-5-vinyl-3-quinolinecarboxylic acid, 0.34 g of 4-methylamino-1,3,3a,4,7,7a-hexahydro-isoindole and 0.18 g of DABCO are refluxed for 2 hours in a mixture of 3 ml of acetonitrile and 1.5 ml of dimethylformamide. At room temperature, the reaction mixture is treated with 20 ml of water, and the product is filtered off with suction, washed with water and dried. 0.5 g of 7-(4-methylamino-1,3,3a,4,7,7a-hexahydro-isoindol-2-yl)-1-cyclopropyl-6,8-difluoro-1,4-dihydro-4-oxo-5-vinyl-3-quinolinecarboxylic acid is obtained.

Melting point: 206°–208° C. (with decomposition)

EXAMPLE 8

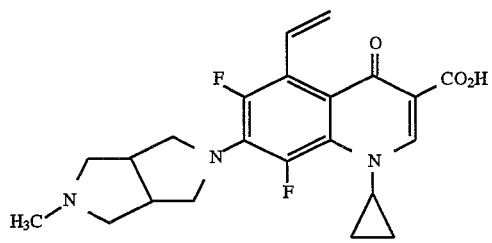

0.46 g of 1-cyclopropyl-6,7,8-trifluoro-1,4-dihydro-4-oxo-5-vinyl-3-quinolinecarboxylic acid, 0.29 g of 4-methyl-octahydropyrrolo[3,4-c]pyrrole and 0.18 g of DABCO are refluxed for 2 hours in a mixture of 3 ml of acetonitrile and 1.5 ml of dimethylformamide. The reaction mixture is subsequently concentrated, and the residue is treated with 10 ml of water. The solid is filtered off with suction, washed with water and dried. 0.5 g of 1-cyclopropyl-6,8-difluoro-1,4-dihydro-7-(5-methyl-hexahydro-pyrrolo[3,4-c]pyrrol-2-yl)-4-oxo-5-vinyl-3-quinolinecarboxylic acid is obtained.

Melting point: 156°–157° C.

EXAMPLE 9

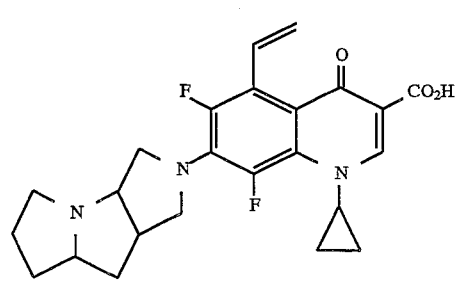

0.93 g of 1-cyclopropyl-6,7,8-trifluoro-1,4-dihydro-4-oxo-5-vinyl-3-quinolinecarboxylic acid, 0.69 g of decahydropyrrolo[3,4-b]pyrrolizine and 0.36 g of DABCO are refluxed for 2 hours in a mixture of 6 ml of acetonitrile and 3 ml of dimethylformamide. At room temperature, the reaction mixture is treated with 20 ml of water, and the solid is filtered off with suction, washed with water and dried. 0.7 g. of 1-cyclopropyl-6,8-difluoro-1,4-dihydro-7-(octahydropyrrolo[3,4-b]pyrrolizin-2-yl)-4-oxo-5-vinyl-3-quinolinecarboxylic acid is obtained.

Melting point: 154°–156° C.

EXAMPLE 10

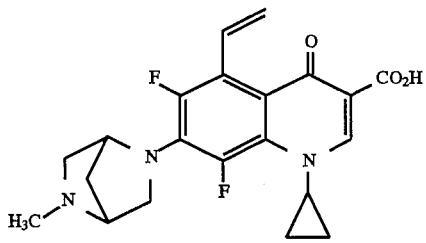

0.93 g of 1-cyclopropyl-6,7,8-trifluoro-1,4-dihydro-4-oxo-5-vinyl-3-quinolinecarboxylic acid, 0.5 g of 2-methyl-2,5-diazabicyclo[2.2.1]heptane and 0.36 g of DABCO are refluxed for 2 hours in a mixture of 6 ml of acetonitrile and 3 ml of dimethylformamide. At room temperature, the reaction mixture is treated with 2 ml of water, and the solid is filtered off with suction, washed with water and dried. 0.9 g of 1-cyclopropyl-6,8-difluoro-1,4-dihydro-7-(2-methyl-2,5-diazabicyclo[2.2.1]hept-5-yl)-4-oxo-5-vinyl-3-quinolinecarboxylic acid is obtained.

Melting point: 199°–201° C.

EXAMPLE 11

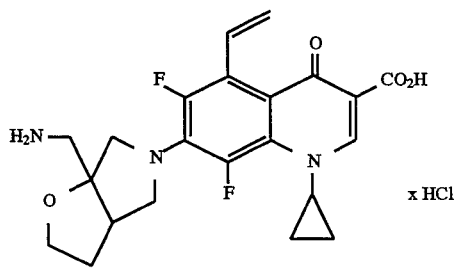

a) 0.46 g of 1-cyclopropyl-6,7,8-trifluoro-1,4-dihydro-4-oxo-5-vinyl-3-quinolinecarboxylic acid, 0.55 g of tert-butoxycarbonyl-(hexahydro-furo[2,3-c]pyrrole-6a-methyl)-amine and 0.18 g of DABCO are refluxed for 2 hours in a mixture of 3 ml of acetonitrile and 1.5 ml of dimethylformamide. After cooling, the reaction mixture is treated with 10 ml of water, and the solid is filtered off with suction, washed with water and dried. 0.6 g of 1-cyclopropyl-6,8-difluoro-1,4-dihydro-4-oxo-7-(6a-tert-butoxycarbonyl-aminomethyl-hexahydro-furo[2,3-c]pyrrol-5-yl)-5-vinyl-3-quinolinecarboxylic acid is obtained.

Melting point: 152°–153° C. (decomp.)

b) 0.53 g of the solid of Part a) are added in portions at 50° C. to 5 ml of 20% aqueous hydrochloric acid. After the mixture has been stirred for 2 hours at room temperature, 2 ml of concentrated aqueous hydrochloric acid are also added. After 2 hours at room temperature, the reaction mixture is concentrated under an oil pump vacuum. The residue is stirred with 4 ml of ethanol, filtered off with suction and dried. 0.33 g of 7-(6a-aminomethylhexahydro-furo[2,3-c]pyrrol-5-yl)-1-cyclopropyl-6,8-difluoro-1,4-dihydro-4-oxo-5-vinyl-3-quinolinecarboxylic acid hydrochloride is obtained.

Melting point: 244°–247° C. (decomp.)

EXAMPLE 12

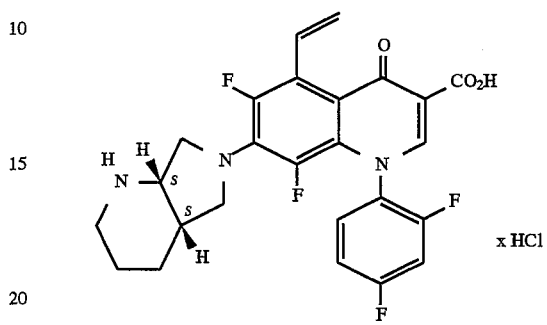

A) 381 mg (1mmol) of 1-(2,4-difluorophenyl)-6,7,8-trifluoro-1,4-dihydro-4-oxo-5-vinyl-3-quinolinecarboxylic acid are suspended in a mixture of 2 ml of acetonitrile and 1 ml of dimethylformamide, and the suspension is treated with 112 mg (1 mmol) of 1,4-diazabicyclo[2.2.2]-octane and 150 mg (1.2 mmol) of S,S-2,8-diazabicyclo[4.3.0]nonane and refluxed for 1 hour. The mixture is concentrated, the residue is stirred with water, and the undissolved precipitate is filtered off with suction, washed with water and recrystallized from glycol monomethyl ether.

Yield: 250 mg (51% of theory) of 7-(S,S-2,8-diazabicyclo[4.3.0]non-8-yl)-1-(2,4-difluorophenyl)-6,8-difluoro-1,4-dihydro-4-oxo-5-vinyl-3-quinolinecarboxylic acid.

Melting point: 212°–215° C. (with decomposition).

B) 150 mg (0.3 mmol) of the betaine of Step A are dissolved in 15 ml of hot semi-concentrated hydrochloric acid. The solution is concentrated, the residue is treated with ethanol, and the hydrochloride is filtered off with suction, washed with ethanol and dried.

Yield: 105 mg (67% of theory) of 7-(S,S-2,8-diazabicyclo[4.3.0]non-8-yl)-1-(2,4-difluorophenyl)-6,8-difluoro-1,4-dihydro-4-oxo-5-vinyl-3-quinolinecarboxylic acid hydrochloride.

Melting point: 224°–228° C. (with decomposition). FAB mass spectrum (positive): m/e 488 [(M+H)$^+$], 470 [(488-H$_2$O$^+$)], 975 [(2M+H)$^+$].

EXAMPLE 13

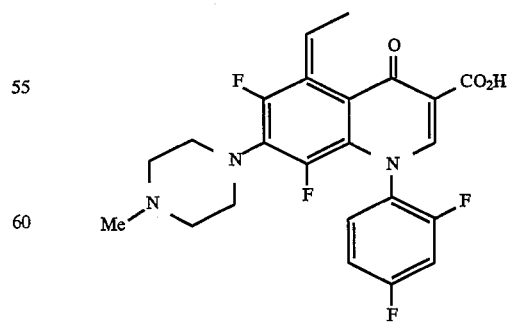

The reaction is carried out analogously to Example 12 A using N-methylpiperazine to give 1-(2,4-difluorophenyl)-6, 8-difluoro-1,4-dihydro-7-(4-methyl-1-piperazinyl)-4-oxo-5-vinyl-3-quinolinecarboxylic acid of melting point 218°–220° C. (with decomposition).

We claim:

1. A quinolone-carboxylic acid derivative of the formula (II):

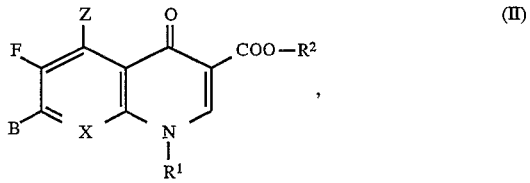

in which $R^1$ represents straight-chain or branched $C_1$–$C_4$-alkyl which is optionally substituted by hydroxyl, halogen or $C_1$–$C_3$-alkoxy, or represents $C_3$–$C_6$-cycloalkyl which is optionally substituted by halogen or $C_1$–$C_3$-alkyl, or $C_2$–$C_4$-alkenyl, furthermore $C_1$–$C_3$-alkoxy, amino, monoalkylamino having 1 to 3 C atoms, dialkylamino having 2 to 6 C atom, or phenyl which is optionally mono- to trisubstituted by halogen, $R^2$ represents hydrogen, alkyl having 1 to 4 carbon atoms or (5-methyl-2-oxo-1,3-dioxol-4-yl)-methyl, Z represents

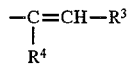

or —C≡C—$R^5$, in which $R^3$ represents hydrogen, $C_1$–$C_3$-alkyl, $C_1$–$C_3$-alkoxy or alkoxymethyl having 1 to 3 C atoms in the alkoxy moiety, $R^4$ represents hydrogen or halogen and $R^5$ represents hydrogen, $C_1$–$C_6$-alkyl which is optionally mono- to trisubstituted by halogen or hydroxyl, or $C_2$–$C_3$-alkenyl, alkoxy having 1 to 3 C atoms, alkoxymethyl having 1 to 3 C atoms in the alkoxy moiety, halogen or trimethylsilyl;

X represents a group CH, C-halogen, C—$OCH_3$, C—$OCHF_2$ or C—$CH_3$; and

B represents halogen.

2. A quinolone-carboxylic acid derivative according to claim 1, in which B represents a halogen selected from the group consisting of fluorine and chlorine.

3. A compound selected from the group consisting of
1-Cyclopropyl-6,7,8-trifluoro-1,4-dihydro-4-oxo-5-vinyl-3-quinolinecarboxylic acid and its esters,
6,7,8-Trifluoro-1-(2,4-difluorophenyl)-1,4-dihydro-4-oxo-5-vinyl-3-quinolinecarboxylic acid and its esters,
1-Cyclopropyl-6,7,8-trifluoro-1,4-dihydro-5-trimethylsilylethinyl-4-oxo-3-quinolinecarboxylic acid and its esters, and
1-Cyclopropyl-5-ethinyl-6,7,8-trifluoro-1,4-dihydro-4-oxo-3-quinolinecarboxylic acid and its esters.

* * * * *